US006022141A

United States Patent [19]

Bass

[11] Patent Number: 6,022,141

[45] Date of Patent: Feb. 8, 2000

[54] APPARATUS AND METHOD FOR REMOTE TEMPERATURE MEASUREMENTS

[75] Inventor: Jay K. Bass, Mountain View, Calif.

[73] Assignee: Qualicon, Wilmington, Del.

[21] Appl. No.: 08/989,907

[22] Filed: Dec. 12, 1997

[51] Int. Cl.[7] .......................... G01K 11/00; G01N 21/76; G01N 25/20

[52] U.S. Cl. .......................... 374/161; 422/52; 422/82.12; 436/147; 436/172

[58] Field of Search .......................... 374/120, 159, 374/161, 162; 422/55, 82.12; 436/147, 172

[56] References Cited

U.S. PATENT DOCUMENTS

| | | | |
|---|---|---|---|
| 4,729,671 | 3/1988 | Asano et al. | 374/160 |
| 5,094,595 | 3/1992 | Larsson et al. | 374/160 |
| 5,224,778 | 7/1993 | Grossman et al. | 374/183 |
| 5,653,539 | 8/1997 | Rosengaus | 374/159 |
| 5,788,374 | 8/1998 | Bur et al. | 374/161 |

*Primary Examiner*—Vit Miska

[57] ABSTRACT

A remote measuring method and apparatus for measuring the temperature of an aqueous solution, particularly useful in monitoring the temperature of a reaction in a microwell, is provided by introducing a dye target and a dye into an aqueous solution; wherein the dye, when bound to the dye target, emits a detectable signal and reproducibly exhibits a temperature dependent signal when appropriately stimulated, stimulating the dye, measuring the resultant signal, and determining the temperature by comparing the measured signal with predetermined temperature related values therefor.

6 Claims, 4 Drawing Sheets

20
20
14
12
22
16
10
18

APPARATUS AND METHOD FOR REMOTE TEMPERATURE MEASUREMENTS

BACKGROUND OF THE INVENTION

This invention relates to the field of temperature measurement and, more particularly, to apparatus and method for remote temperature measurements, particularly of reactions in microwells, and for calibration of heating means.

Work done in the microelectronics industry has resulted in a body of techniques that have come to be known generally as "micromachining". A decade ago this was just beginning to burgeon (see Angel et al., *Scientific American*, Vol. 248, 44–55, 1983). Today miniature processing devices incorporated into chip structures are fairly common and components are sized on a microscale which by definition is between 0.1 μm and 500 μm. Such small apparatus is of great benefit in microbiology. Assays, using micro processing methods, permit the use of small volume samples held in miniature containers (hereinafter "microwells") thereby improving heat transfer, mixing and reaction efficiency, reducing costs by stocking smaller quantities of expensive reagents and permitting greatly reduced and less costly sample volumes. Single-use, inexpensive and disposable structures are avidly sought.

Capillary electrophoresis, for example, is a field of great activity, as is the development of small scale methods for polymerase chain reaction (PCR). Processing channels for capillary electrophoresis may be on the order of 15 μm deep by 100 μm wide and processing wells for PCR may be about 0.5 mm deep and 2 mm square to hold samples with a volume of about 2 μL. These microwells must be supplied with heating and cooling means and the temperatures in the wells must be controlled with precision.

PCR involves repeated cycling between several elevated temperatures (see U.S. Pat. Nos. 4,683,195 and 4,693,202). As a result, measurement and control of temperature is paramount. When performed on a microscale, measurement of the temperature in the micro wells becomes exceedingly difficult. Thermometers are too large. Thermocouple probes, thermistors and resistance temperature devices (RTDs), ordinarily used in calibrating and monitoring temperatures in small spaces, are large enough in comparison to the volume involved in a microwell to intrude on the test accuracy. While it is possible to fabricated these devices as an integral part of the apparatus to obviate the intrusion, they are expensive to calibrate and only provide temperature of a local region since they are restricted to an edge or side of a well. In addition, because the temperatures involved are below 100° C., remote sensing methods which rely on infrared emanations are not effective.

Thus, it is an object of this invention to provide a remote sensing method and apparatus for measuring and/or calibrating temperatures in the range around or below 100° C. in microwells. While the inventive method is particularly adapted for use with microwells, it will be appreciated that the method may be used with a variety of apparatus and thus is not limited to this single use.

SUMMARY OF THE INVENTION

The problems of the prior art are solved by the instant invention which provides remote sensing for an aqueous liquid.

In one aspect, the invention provides a remote measuring method for measuring the temperature of an aqueous solution comprising the steps of:

(a) introducing a dye target and a dye into an aqueous solution; wherein the dye, when bound to the dye target, emits a detectable signal and reproducibly exhibits a temperature dependent signal when appropriately stimulated, (b) stimulating the dye, (c) measuring the resultant signal, and (d) determining the temperature by comparing the measured signal with predetermined temperature related values therefor.

In another aspect, the invention provides an apparatus for remotely measuring the temperature in a microwell, the apparatus comprising, in combination:

(a) a substrate having a processing microwell and a temperature measuring microwell therein in close proximity to one another;

(b) means for the controlled heating and cooling of said processing microwell and said temperature measuring microwell;

(c) means to stimulate a dye contained in said temperature measuring microwell; and (d) a detector.

DETAILED DESCRIPTION OF THE EMBODIMENTS

Figure 1:
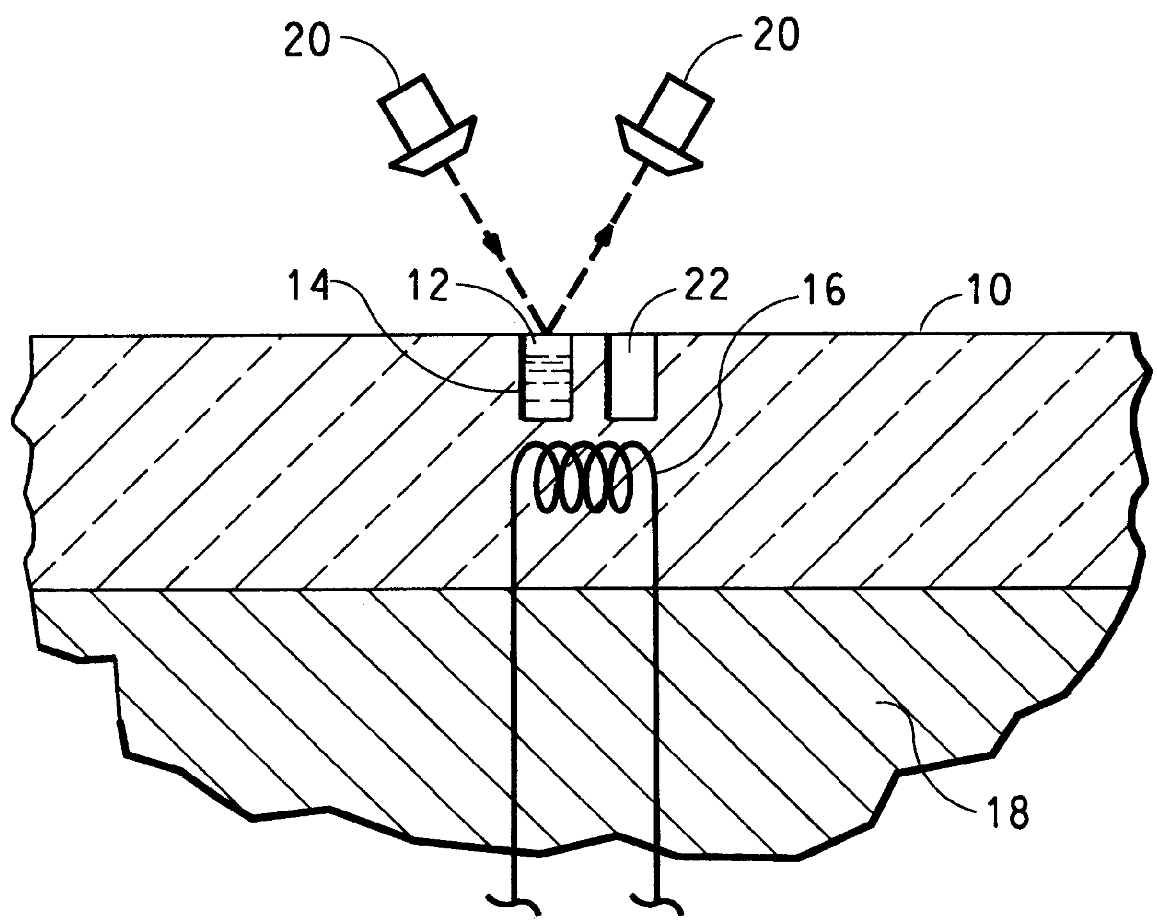
FIG. 1 is a schematic representation of the remote temperature measuring apparatus of the invention.

With reference to FIG. 1, an apparatus for use in measuring the temperature in a microwell is illustrated. As seen in FIG. 1, a substrate 10 is provided with two microwells, 12, 22, disposed in close proximity to one another. The substrate 10 may be made of silicon, glass, or the like as is known and the microwells may be formed by etching or micromachining techniques.

The apparatus includes means for heating and cooling the microwells 12, 22. In the embodiment illustrated, an electrical resistance heater 16 is shown for heating the microwells and a heat sink 18 is shown for reducing the temperature of the microwells, preferably used in conjunction with a cooling medium such as air swept across the exposed surfaces of the substrate 10 and/or the heat sink 18. Any other means for heating and cooling the wells in accordance with the particular test protocol can be used in practicing the invention.

The apparatus also includes means for stimulating the aqueous solution containing the dye and dye target and for detecting the temperature-dependent signal generated thereby. In the embodiment shown, a fluorometer 20 excites the dye in solution 14 and measures the resultant fluorescence in units appropriate to the instrument (hereinafter fluorescent intensity units or "FIU"). By comparing the resultant FIU with values predetermined under controlled conditions, the temperature in well 12 becomes known with precision without the presence of any mechanical probe in the well or any contact with the solution 14. The excitation and emission is preferably provided by separate fiber bundles, but suitable alternatives include using a single bifurcated fiber bundle for excitation and emission at a single end or the use of microscope optics (dichroic mirror, lenses) to also provide excitation/emission from a single side.

The process of the present invention essentially comprises charging a microwell with an aqueous solution of a dye and a dye target, stimulating the dye to create a signal, and then measuring the signal (e.g., fluorescence) and comparing it to a set of calibration standards to determine the temperature. The process is particularly useful for microwell reactions that involve temperatures below 100° C.

The dye target can be a selected sequence of double stranded DNA ("dsDNA"), RNA, or protein. Double stranded DNA is most preferred as the dye target. The dye is one that is capable of generating a reproducible, detectable, temperature-dependent signal when it is (i) bound to the dye target and (ii) stimulated by a suitable energy source (e.g., ultraviolet light). The signal produced by the dye under such conditions is distinct from any signal emitted by unbound dye or by dye bound to a competing target (e.g., single stranded DNA). Further, the emitted signal is reproducibly temperature dependent within the temperature range of interest, i.e. under 100° C. Temperature-dependent, fluorescing, intercalating dyes are particularly preferred.

The aqueous solution of dye and dye target is preferably added directly to the microwell containing the sample as an active component of the detection function in an assay. However, in some situations this is not advised because of potential interference of the dye or dye target with the particular test. In such situations, the aqueous solution of dye and dye target is added to a companion microwell, that is, a microwell in close proximity to the test microwell and heated and cooled simultaneously with the test microwell.

A calibration method can be used in which the heating/cooling means for a microwell is calibrated by charging the well with a dsDNA/intercalating dye combination as described and using the fluorescence excited and measured versus known, temperature-dependent-fluorescence properties to adjust and set the temperature control means.

There are two characteristics of using the dye: 1) it saves the need for performing a calibration on each part, and 2) it gives an average temperature within the well.

Using dsDNA as the dye target provides a system with an upper temperature limit because the bonds between the double strands will break, resulting in two single strands below 100° C. in aqueous solution. This phenomenon is referred to herein as "melting" the DNA. The precise temperature range at which DNA will melt depends on the particular sequence employed. The melting is typically a reversible process, such that cooling the solution will result in the dsDNA being re-formed. It is possible to lock the DNA strands, thus permitting the use of this invention at temperatures above the "melting" point of the DNA, by adding an intercalating agent, such as IP-10 (available from HRI Assoc. Inc.), and exposing the solution to ultraviolet light. Proteins are also susceptible to temperature limitations but, unlike dsDNA, most proteins become irreversibly denatured at elevated temperatures. Thus, the use of proteins as dye targets is not particularly preferred.

The amount of dye and dye target used in the aqueous solution will, of course, vary depending on the particular dye/dye target combination employed, the temperature range being monitored, the sensitivity of the detection system, and similar variables. One skilled in the art should readily be able to determine the appropriate concentrations without undue experimentation.

EXAMPLES

Figure 2:
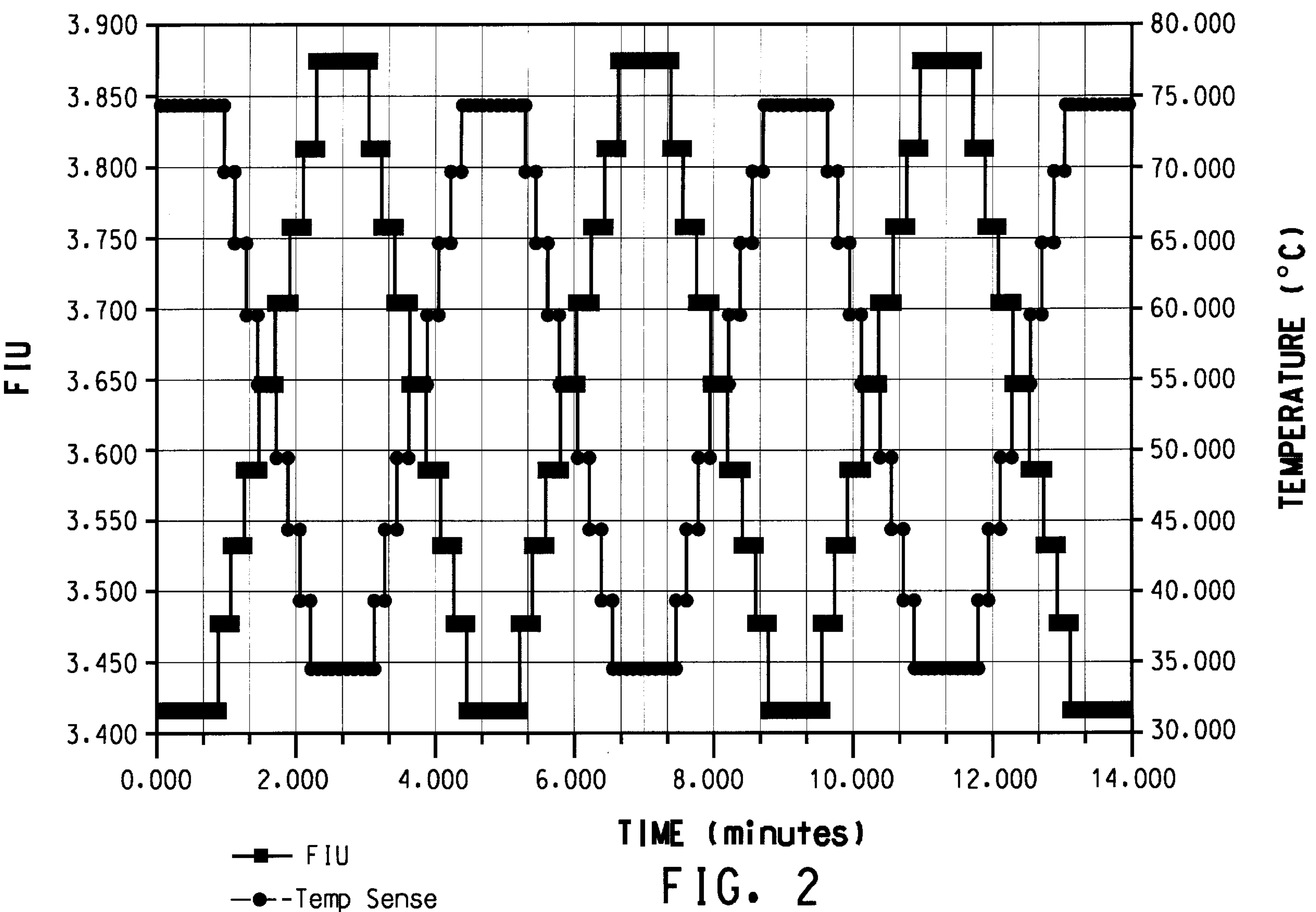
FIG. 2 is a plot of fluorescence of a temperature-dependent dye as a function of time and temperature as the temperature is cycled through high and low values.
Figure 3:
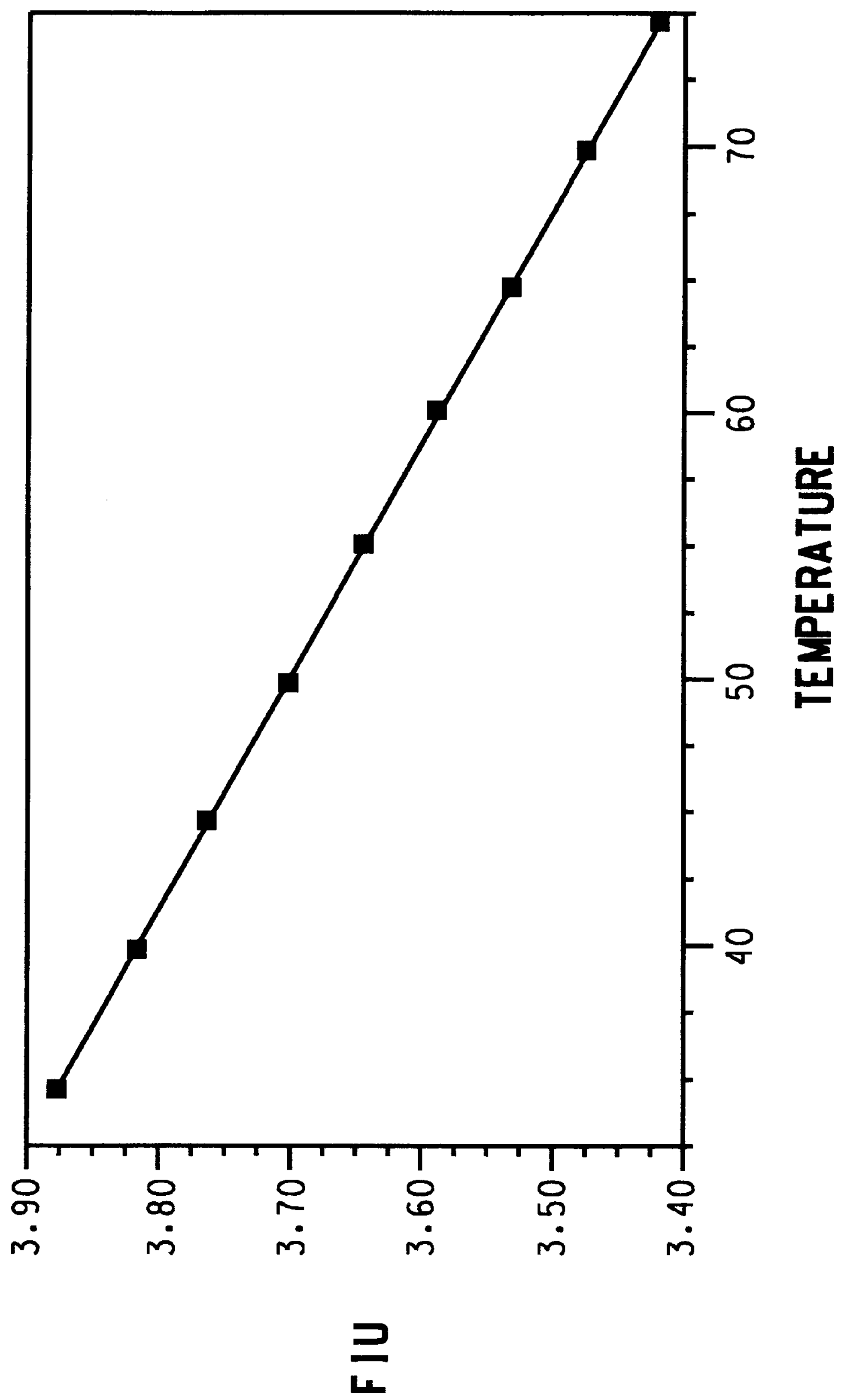
FIG. 3 is a plot of the data of FIG. 2 showing fluorescence as a function of temperature.

An aqueous solution was prepared comprising 2 ng/$\mu$l of a 500 base pair dsDNA and 3 $\mu$M of an intercalating dye (Yo-Pro-1™, Molecular Probes Inc.). 2 $\mu$L of the aqueous solution was introduced into a suitably sized microwell in a silicon substrate. The microwell was heated electrically by a resistance heater and cooled by circulating air across the silicon surface. Temperature and time were controlled by computer. Temperature in the microwell was measured by an RTD built into the bottom of the well and the fluorescence of the solution was monitored by a fluorometer. The temperature was held for 60 seconds at 35° C. and for 60 seconds at 75° C. The data are shown in the plot in FIG. 2.

Figure 4:
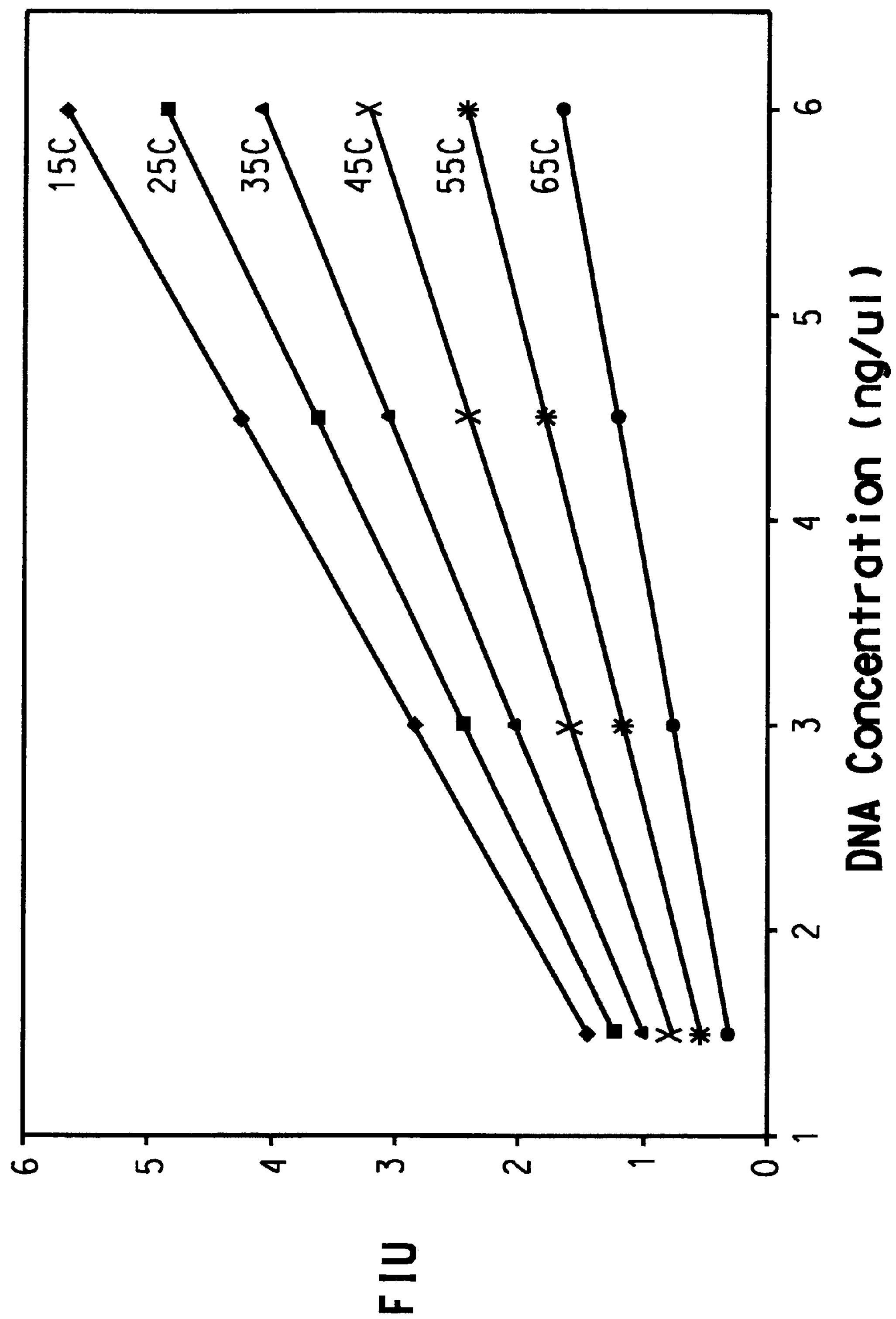
FIG. 4 is a plot of fluorescence of a temperature-dependent dye as a function of temperature and dye target concentration.

Experiments also established that the measured fluorescence in FIU was linear as a function of DNA concentration at various temperature settings. A 500 base pair dsDNA fragment was diluted in lysis buffer (50 mM Tris-HCl, pH=8.3, 50 mM KCl and 3 mM $MgCl_2$) with 3 $\mu$M of Yo-Pro-1™ dye. Dilutions of 1.5, 3.0, 4.5 and 6.0 ng/$\mu$l were made and 50 $\mu$l of each dilution was placed in 16 PCR tubes (2 strips of 8 tubes each) and the tubes were placed in a thermal cycler (Perkin Elmer Model 9600). The tubes were allowed to equilibrate at the desired temperature and the fluorescence was measured, one tube at a time, in a BAX™ fluorometer (Qualicon, Inc., Wilmington, Del.). The data obtained are plotted in FIG. 4. Values were recorded as shown and are the average of 16 tubes at each dilution.

The ratios of 15C FIU value to 65 FIU value for different concentrations of DNA are 0.286 for 1.5 ng/$\mu$l, 0.285 for 3 ng/$\mu$l, 0.286 for 4.5 ng/$\mu$l and 0.288 for 6ng/$\mu$l establishing linearity with mass and reproducibility of the temperature measuring technique independent of mass. As a result, given the FIU at a specific temperature one could calculate the FIU at another temperature without knowing the DNA concentration within the sample. These linear results add to convenience but the method plainly would operate with a nonlinear response provided each cycle repeats the others.

What is claimed is:

1. A remote measuring method for measuring the temperature of an aqueous solution comprising the steps of:

(a) introducing a dye target and a dye into an aqueous solution; wherein the dye, when bound to the dye target, emits a detectable signal and reproducibly exhibits a temperature dependent signal when appropriately stimulated, (b) stimulating the dye, (c) measuring the resultant signal, and (d) determining the temperature by comparing the measured signal with predetermined temperature related values therefor.

2. The method of claim 1 wherein the dye target is a selected dsDNA and the dye is an intercalating dye.

3. The method of claim 1 wherein the aqueous solution is contained in a microwell which is in close thermal proximity and equality to a microwell in which a process of interest is performed.

4. The method of claim 3 wherein the process of interest is an assay including PCR processing.

5. A method for calibrating controlled heating and or cooling means associated with a microwell comprising carrying out the method of claim 1 in said microwell and adjusting said heating and or cooling control means according to the results attained thereby.

6. Apparatus for performing the method of claim 1 comprising a substrate having a processing microwell therein and in close proximity thereto a temperature measuring microwell, both wells sharing controlled heating and cooling means, and means to stimulate and measure the signal.

* * * * *